United States Patent
Ralph

(10) Patent No.: US 11,590,236 B2
(45) Date of Patent: Feb. 28, 2023

(54) COMPOSITIONS AND METHODS FOR ALTERING MACROPHAGE PHENOTYPE

(71) Applicant: Navidea Biopharmaceuticals, Inc., Dublin, OH (US)

(72) Inventor: David A. Ralph, Columbus, OH (US)

(73) Assignee: Navidea Biopharmaceuticals, Inc., Dublin, OH (US)

( * ) Notice: Subject to any disclaimer, the term of this patent is extended or adjusted under 35 U.S.C. 154(b) by 0 days.

(21) Appl. No.: 16/832,620

(22) Filed: Mar. 27, 2020

(65) Prior Publication Data

US 2020/0306381 A1 Oct. 1, 2020

Related U.S. Application Data

(60) Provisional application No. 62/824,853, filed on Mar. 27, 2019.

(51) Int. Cl.

| | |
|---|---|
| *A61K 47/61* | (2017.01) |
| *A61K 31/704* | (2006.01) |
| *A61K 31/337* | (2006.01) |
| *A61P 35/00* | (2006.01) |
| *A61K 31/517* | (2006.01) |
| *A61K 31/675* | (2006.01) |
| *A61K 33/34* | (2006.01) |
| *A61K 31/7068* | (2006.01) |

(52) U.S. Cl.
CPC ............ *A61K 47/61* (2017.08); *A61K 31/337* (2013.01); *A61K 31/517* (2013.01); *A61K 31/675* (2013.01); *A61K 31/704* (2013.01); *A61K 31/7068* (2013.01); *A61K 33/34* (2013.01); *A61P 35/00* (2018.01)

(58) Field of Classification Search
CPC ..... A61K 47/61; A61K 31/337; A61K 31/517
See application file for complete search history.

(56) References Cited

U.S. PATENT DOCUMENTS

| | | | | |
|---|---|---|---|---|
| 6,218,367 B1* | 4/2001 | Jacob | ..................... | C07H 15/26 514/25 |
| 9,139,652 B2 | 9/2015 | Haegel et al. | | |
| 2009/0258025 A1 | 10/2009 | Godowski et al. | | |
| 2015/0023876 A1* | 1/2015 | Cope | .................. | A61K 49/0054 424/1.73 |
| 2018/0015187 A1 | 1/2018 | Cope | | |
| 2021/0000920 A1* | 1/2021 | Quay | ................... | A61K 9/5123 |

FOREIGN PATENT DOCUMENTS

WO 2018213808 A1 11/2018

OTHER PUBLICATIONS

Van Dalen et al., "Molecular Repolarisation of Tumor-Associated Macrophages", "Molecules", Dec. 20, 2018, pp. 1-25, No. 24.

Guiducci, C., et al., Redirecting in vivo elicited tumor infiltrating macrophages and dendritic cells towards tumor rejection. Cancer Res, 2005. 65(8): p. 3437-46.

Chang, L.S., et al., Toll-like receptor 9 agonist enhances anti-tumor immunity and inhibits tumor-associated immunosuppressive cells numbers in a mouse cervical cancer model following recombinant lipoprotein therapy. Mol Cancer, 2014. 13: p. 60.

Feng, M., et al., Macrophages eat cancer cells using their own calreticulin as a guide: roles of TLR and Btk. Proc Natl Acad Sci U S A, 2015. 112(7): p. 2145-50.

Genard, G., S. Lucas, and C. Michiels, Reprogramming of Tumor-Associated Macrophages with Anticancer Therapies: Radiotherapy versus Chemo- and Immunotherapies. Front Immunol, 2017. 8: p. 828. 19 pages.

Wanderley, C.W., et al., Paclitaxel Reduces Tumor Growth by Reprogramming Tumor-Associated Macrophages to an M1 Profile in a TLR4-Dependent Manner. Cancer Res, 2018. 78(20): p. 5891-5900.

Movahedi, K., et al., Different tumor microenvironments contain functionally distinct subsets of macrophages derived from Ly6C(high) monocytes. Cancer Res, 2010. 70(14): p. 5728-39.

Hannesdottir, L., et al., Lapatinib and doxorubicin enhance the Stat1-dependent antitumor immune response. Eur J Immunol, 2013. 43(10): p. 2718-29.

Coscia, M., et al., Zoledronic acid repolarizes tumour-associated macrophages and inhibits mammary carcinogenesis by targeting the mevalonate pathway. J Cell Mol Med, 2010. 14(12): p. 2803-15.

Peranzoni, E., et al., Macrophages impede CD8 T cells from reaching tumor cells and limit the efficacy of anti-PD-1 treatment. Proc Natl Acad Sci USA, 2018. 115(17): p. E4041-e4050.

Azad, A.K., et al., gamma-Tilmanocept, a New Radiopharmaceutical Tracer for Cancer Sentinel Lymph Nodes, Binds to the Mannose Receptor (CD206). J Immunol, 2015, 11 pages.

Kryczek, I., et al., B7-H4 expression identifies a novel suppressive macrophage population in human ovarian carcinoma. J Exp Med, 2006. 203(4): p. 871-81.

Cope, FO et al., "The Inextricable Axis of Targeted Diagnostic Imaging and Therapy: An Immunological Natural History Approach," Nucl Med Biol. Mar. 2016 43:3 215-225, 31 pages.

Ganguly, A. et al., "The role of a Schiff base scaffold N-(2-hydroxy acetophenone) glycinate-in overcoming multidrug resistance in cancer," European Journal of Pharmaceutical Sciences 51 (2014) 96-109.

Azad, A. et al., "Mannose receptor (CD206)-mediated imaging in sentinel lymph node localization," Clin Transl Imaging (2015) 3:237-245, 9 pages.

(Continued)

*Primary Examiner* — Pancham Bakshi

(74) *Attorney, Agent, or Firm* — Sean D. Solberg; Tina G. Yin Sowatzke

(57) ABSTRACT

Disclosed are methods and compositions for repolarizing a tumor associated macrophage (TAM) from M2 to M1 comprising administering to a subject in need thereof an effective dose of a compound comprising a dextran backbone and one or more CD206 targeting moieties conjugated thereto. In certain aspects, the compound further comprises a therapeutic agent selected from: paclitaxel, gemcitabine, lapatinib, and doxorubicin. In further aspect, the therapeutic agent comprises a chelator and at least one metal ion. In certain implementations, the at least one metal ion comprises at least one Cu(II) ions.

9 Claims, 9 Drawing Sheets

(56) References Cited

OTHER PUBLICATIONS

Junankar, S. et al., "Real-time Intravital Imaging establishes Tumour-associated Macrophages as the Extraskeletal Target of Bisphosphonate Action in Cancer," Cancer Discov. Jan. 2015; 5(1):35-42, 15 pages.
Leonard, F. et al., "Macrophage Polarization Contributes to the Anti-Tumoral Efficacy of Mesoporous Nanovectors Loaded with Albumin-Bound Paclitaxel," Frontiers in Immunology, Jun. 2017, vol. 8, Art. 693, 14 pages.
Pal, R et al., "Noble metal nanoparticle-induced oxidative stress modulates tumor associated macrophages (TAMs) from an M2 to M1 phenotype: an invtro approach," International Immunopharmacology 38 (2016) 332-341.
Rogers, T. et al., "Tumour macrophages as potential targets of bisphosphonates," Journal of Translational Medicine (2011)9:177, 17 pages.
Tarasova, N. et al., "Cytotoxic and Proinflammatory Effects of Metal-Based Nanoparticles on THP-1 Monocytes Characterized by Combined Proteomics Approaches," Journal of Proteome Research (2017) 16, 689-697.
Triboulet, S. et al., "Molecular Responses of Mouse Macrophages to Copper and Copper Oxide Nanoparticles Inferred from Proteomic Analyses," American Society of Biochemistry & Molecular Biology Inc., Molecular & Cellular Proteomics 12.11 (2013), 3108-3122.
Yamaguchi, T. et al., "Low-dose paclitaxel suppresses the induction of M2 macrophages in gastric cancer," Oncology Reports 37: (2017) 3341-3350.
Santoni, M., et al., Triple negative breast cancer: Key role of Tumor-Associated Macrophages in regulating the activity of anti-PD-1/PD-L1 agents. Biochim Biophys Acta, 2018. 1869(1): p. 78-84.
Aras, S. and M.R. Zaidi, TAMeless traitors: macrophages in cancer progression and metastasis. Br J Cancer, 2017. 117(11): p. 1583-1591.
Ngambenjawong, C., H.H. Gustafson, and S.H. Pun, Progress in tumor-associated macrophage (TAM)-targeted therapeutics. Adv Drug Deliv Rev, 2017.
Zheng, X., et al., Redirecting tumor-associated macrophages to become tumoricidal effectors as a novel strategy for cancer therapy. Oncotarget, 2017 8(29): p. 48436-48452.
Costa da Silva, M., et al., Iron Induces Anti-tumor Activity in Tumor-Associated Macrophages. Front Immunol, 2017. 8: p. 1479.
Zhou, Y., et al., Iron overloaded polarizes macrophage to proinflammation phenotype through ROS/acetyl-p53 pathway. Cancer Med, 2018. 7(8): p. 4012-4022.
Gao, H., et al., The Role of Zinc and Zinc Homeostasis in Macrophage Function. J Immunol Res, 2018. 2018: p. 6872621.
Riemschneider, S., M. Herzberg, and J. Lehmann, Subtoxic Doses of Cadmium Modulate Inflammatory Properties of Murine RAW 264.7 Macrophages. Biomed Res Int, 2015. 2015: p. 295303.
Mookerjee, A., et al., A novel copper complex induces ROS generation in doxorubicin resistant Ehrlich ascitis carcinoma cells and increases activity of antioxidant enzymes in vital organs in vivo. BMC Cancer, 2006. 6: p. 267.
Chakraborty, P., et al., Reprogramming of TAM toward proimmunogenic type through regulation of MAP kinases using a redox-active copper chelate. J Leukoc Biol, 2012. 91(4): p. 609-19.
Chatterjee, S., et al., A novel copper chelate modulates tumor associated macrophages to promote anti-tumor response of T cells. PLoS One, 2009. 4(9): p. e7048.
Sato-Kaneko, F., et al., Combination immunotherapy with TLR agonists and checkpoint inhibitors suppresses head and neck cancer. JCI Insight, 2017. 2(18).
Banciu, M. et al., "Investigation into the Role of Tumor-Associated Macrophages in the Antitumor Activity of Doxil," Pharmaceutical Research, vol. 25, No. 8, Aug. 2008, pp. 1948-1955.
Guo, Z. et al., "Combined Tradectedin and anti-PD1 antibody produces a synergistic antitumor effect in a murine model of ovarian cancer," J. Transl. Med. (2015) 13:247, 13 pages.
Petty, A. et al., "Tumor-associated macrophages: implications in cancer immunotherapy," Immunotherapy (2017) 9(3) pp. 289-302.
Mantovani, A. et al., "Tumor-Associated Macrophages as Treatment Targets in Oncology," Nat. Rev. Clin. Oncol. Jul. 2017; 14(7): 399-416, 34 pages.
Hwang, J. et al., "Dextran-b-poly(L-histidine) copolymer nanoparticles for pH-responsive drug delivery to tumor cells," International Journal of Nanomedicine 2013:8, pp. 3197-3207.
Chakraborty, P. et al., "A copper chelate selectively triggers apoptosis in myeloid-derived suppressor cells in a drug-resistant tumor model and enhances anti-tumor immune response," Immunopharmacol Immunotoxicol, 2014; 36(2) pp. 165-175.

* cited by examiner

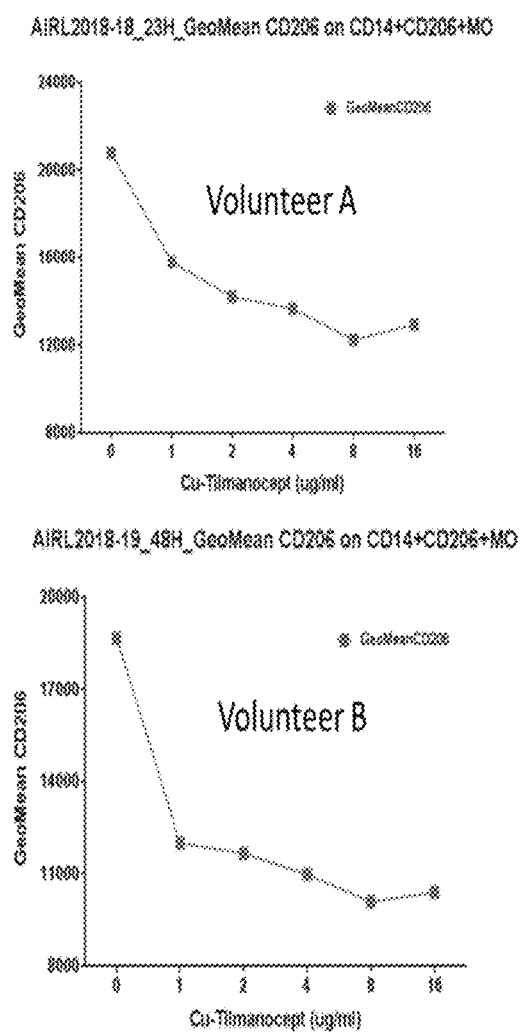
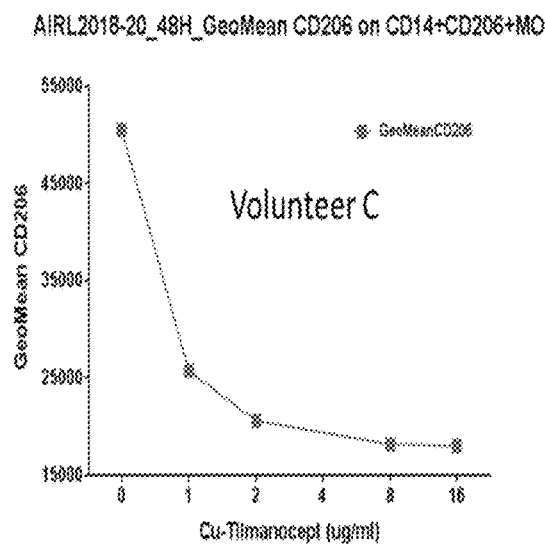
Figure 1. Decrease in Geometric Mean CD206 Fluorescence of the M2 macrophages Derived from 3 Volunteers Following Exposure to Increasing Concentrations of Cu(II)-Tilmanocept for 23 hours (Volunteer A) or 48 hours (Volunteers B and C)

Figure 3. Changes in expression of CD80 and CD86 by M2 macrophages upon increasing exposure to Cu(II)-tilmanocept for either 23 hours (red) or 48 hours (blue and green).

Figure 4. Changes in expression of CD80 and CD86 normalized to changes in CD206 expression in CD206+ M2 macrophages treated with Cu(II)-tilmanocept at increasing concentrations for either 23 or 48 hours.

Normalize MO CD86 expression data of 6 experiments from 4 donors

Normalize MO CD163 expression data of 7 experiments from 4 donors

Normalize MO CD64 expression data of 5 experiments from 4 donors

Normalize MO CD206 regulation data of 8 experiments from 5 donors

COMPOSITIONS AND METHODS FOR ALTERING MACROPHAGE PHENOTYPE

CROSS-REFERENCE TO RELATED APPLICATION(S)

This application claims priority to U.S. Provisional Application No. 62/824,853 filed Mar. 27, 2019 and entitled "Altering the Phenotype of Macrophages with CD206 Targeted Drug Delivery Vehicles Carrying Appropriate Pharmacologically Active Payloads," which is hereby incorporated by reference in its entirety under 35 U.S.C. § 119(e).

BACKGROUND OF THE INVENTION

Cancer is the second leading cause of deaths in the USA, accounting for nearly one of every four deaths. Cancer is characterized by the unregulated growth and cell division of cancer cells. However, cancers benefit enormously from chronic maladaptive immune responses to tumors and macrophages are a key mediator of that maladaptive response. In general, macrophages respond to various stimuli in their local microenvironment by altering their expression patterns for many genes, potentially hundreds. Such phenotypically altered macrophages are said to be activated macrophages. Depending upon which stimuli a macrophage is responding to, a wide range of activated phenotypic states can be attained. Among those genes that are differentially expressed upon macrophage activation are cell surface markers (such as the macrophage mannose receptor, CD206) and various cytokines, enzymatic pathways leading to the generation of reactive oxygen species (ROS), and other signaling molecules that can regulate the behavior of other components of the immune system, such as T lymphocytes (T-cells). When first described, activated macrophages were divided into two phenotypes: classically activated, called M1, which is highly proinflammatory, and alternatively activated, called M2, which is immunosuppressive and promotes wound healing. It is now understood that a strictly dichotomous classification of activated macrophage phenotypes is overly simplistic and does not represent the true plasticity of macrophage responses to stimuli from their microenvironments; however, the concept that activated macrophages can influence a local immune response by being either proinflammatory (M1-like) or immunosuppressive (M2-like) continues to have utility when describing the role of macrophages in various pathological states.

Tumor associated macrophages (TAMs) are abundant in tumors and highly significant contributors to the maladaptive immune response associated with cancer. While both M1-like and M2-like TAMs are known, the large majority of TAMs residing in or near established tumors are immunosuppressive, M2-like activated macrophages. Importantly, these M2-like TAMs are frequently identified in immunohistochemical evaluations of tumors by their high expression of CD206 (i.e. are CD206+). M2-like TAMs suppress T-cells by expressing IL-10, TGF-β, and PD-L1, and promote tumor angiogenesis and metastases.

There is a need in the art for compositions and methods that induce the phenotypic change of the M2-like TAMs to M1-like TAMs in order to treat cancer with greater efficacy and lower toxicity.

BRIEF SUMMARY OF THE INVENTION

Disclosed herein are compositions and methods for repolarizing a tumor associated macrophage (TAM) from M2 to M1. In certain embodiments, methods comprise administering to a subject in need thereof an effective dose of a compound comprising: a dextran backbone and one or more CD206 targeting moieties conjugated thereto. In certain exemplary embodiments, the compound comprises a compound of Formula (I):

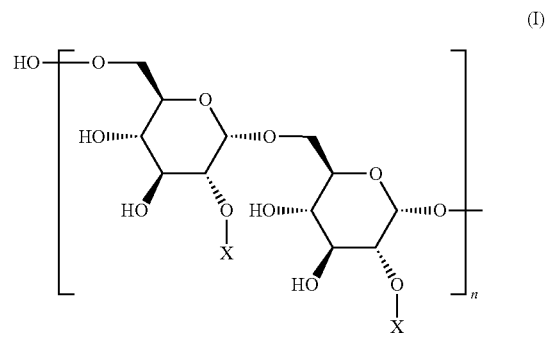

wherein
each X is independently H, L1-A, or L2-R;
each L1 and L2 are independently linkers;
each A independently comprises a therapeutic agent or H;
each R independently comprises a mannose-binding C-type lectin receptor targeting moiety or H;
and n is an integer greater than zero; and
wherein at least one R comprises a mannose-binding C-type lectin receptor targeting moiety selected from the group consisting of mannose, fucose, and n-acetylglucosamine and at least one A comprises a therapeutic agent.

According to certain further embodiments, the therapeutic agent is selected from: paclitaxel, gemcitabine, lapatinib, and doxorubicin. In further embodiments, the therapeutic agent is doxorubicin. In certain aspects, administration of the composition to the subject has reduced toxicity relative to an equivalent dose of the therapeutic agent not conjugated to the composition.

According to certain embodiments the therapeutic agent is a bisphosphonate. In further embodiments, the bisphosphonate is zoledronic acid.

In certain aspects, therapeutic agent comprises a chelator and at least one metal ion. In certain implementations, the at least one metal ion comprises at least one Cu(II) ions. In further aspects, the at least one Cu(II) ions comprise about 4 Cu(II) ions. In further aspects, the at least one Cu(II) ion is between about 1 Cu(II) ion and a number of Cu(II) ions equal to the number of chelator moieties.

In certain aspects, the compound is administered in conjunction with at least one other therapy or treatment. In certain embodiments, the at least one other treatment or therapy is a chemotherapy, radiation therapy, or immunotherapy. According to certain implementations, the at least one other treatment or therapy is anti-CTLA4 immunotherapy. In exemplary implementations, the combined administration of the compound and the at least one treatment or therapy is synergistically effective relative to administration of either alone.

According to certain alternative embodiments, the compound does not comprise a therapeutic agent.

Further disclosed herein is compound for repolarizing a TAM from M2 to M1 comprising a compound of Formula (I):

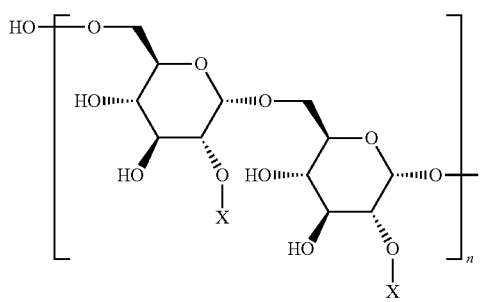

(I)

wherein
each X is independently H, L1-A, or L2-R;
each L1 and L2 are independently linkers;
each A independently comprises a therapeutic agent or H;
each R independently comprises a mannose-binding C-type lectin receptor targeting moiety or H;
and n is an integer greater than zero; and
wherein at least one R comprises a mannose-binding C-type lectin receptor targeting moiety selected from the group consisting of mannose, fucose, and n-acetylglucosamine and at least one A comprises a therapeutic agent, wherein the therapeutic agent comprises a chelator and at least one Cu(II) ion.

In certain implementations, at least one L1 comprises —(CH2)pS(CH2)$_q$-NH—, wherein p and q are integers from 0 to 5.

In further aspects, at least one L2 is a C2-12 hydrocarbon chain optionally interrupted by up to three heteroatoms selected from the group consisting of O, S and N.

In yet further aspects, at least one L2 comprises —(CH2)pS(CH2)$_q$-NH—, wherein p and q independently are integers from 0 to 5.

Further disclosed herein is a compound for repolarizing a TAM from M2 to M1 comprising a compound of Formula (I):

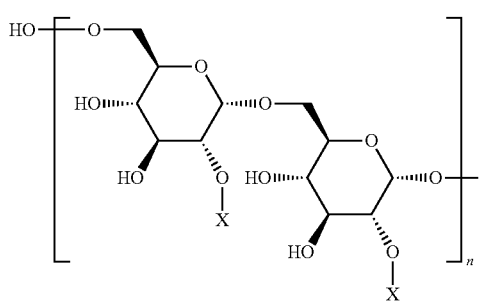

(I)

wherein each X is independently H, L1-A, or L2-R;
each L1 and L2 are independently linkers;
each A independently comprises a therapeutic agent or H;
each R independently comprises a mannose-binding C-type lectin receptor targeting moiety or H;
and n is an integer greater than zero; and
wherein at least one R comprises a mannose-binding C-type lectin receptor targeting moiety selected from the group consisting of mannose, fucose, and n-acetylglucosamine and at least one A comprises a therapeutic agent, wherein the therapeutic agent comprises doxorubicin.

In certain implementations, each L1 is a hydrazone linker.

According to further implementations, the ratio of mannose-binding C-type lectin receptor targeting moieties to doxorubicin moieties is about 18.5 to about 1.5. In still further implementations, the dextran backbone is about 10 kD.

Further disclosed herein is a method of treating an infectious disease comprising administering to a subject in need thereof an effective amount of any of the compounds disclosed herein of any, wherein the compound is administered at a dose sufficient to induce M2 macrophages to repolarize to M1 macrophages. In certain implementations, the infectious disease is selected from: Dengue Fever, tuberculosis, leishmaniasis, and Human Immunodeficiency Virus.

BRIEF DESCRIPTION OF THE FIGURES

FIG. 1 shows graphs of the decrease in geometric mean CD206 fluorescence of the M2 macrophages derived from 3 volunteers following exposure to increasing concentrations of Cu(II)-Tilmanocept for 23 hours (Volunteer A) or 48 hours (Volunteers B and C).

DETAILED DESCRIPTION

Figure 2:
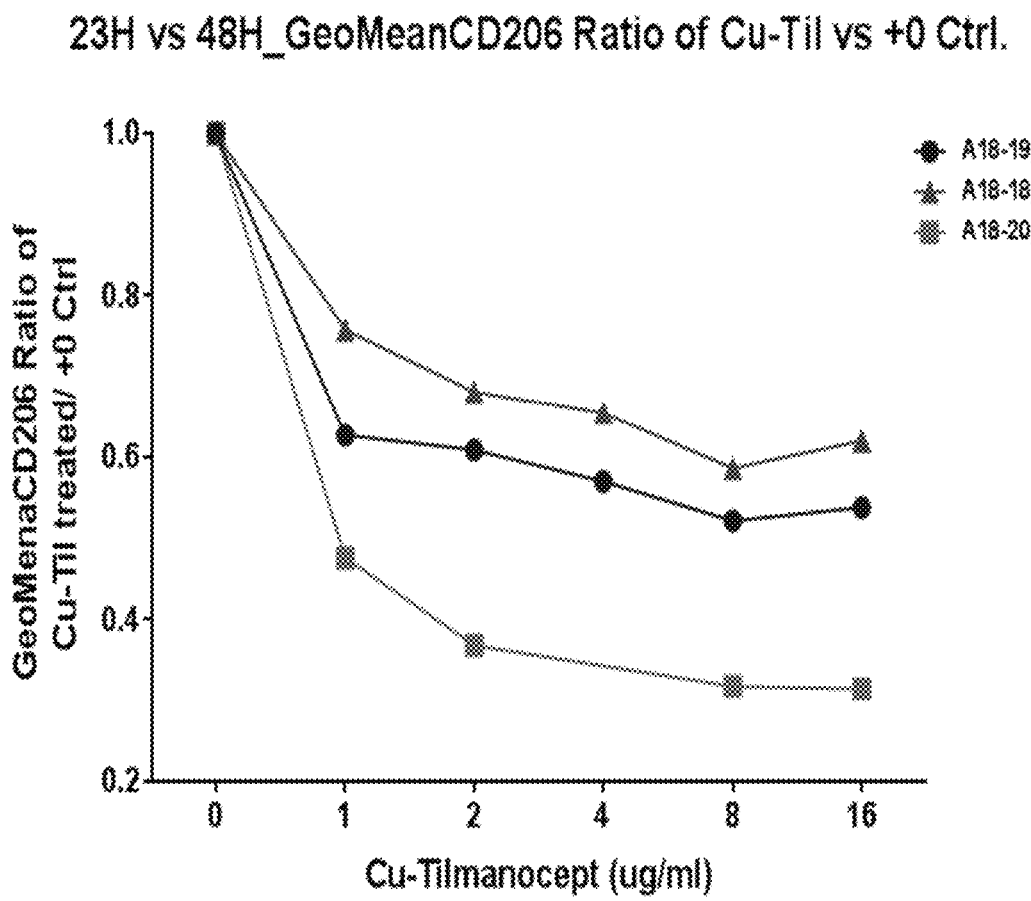
FIG. 2 shows a graph of the geometric mean CD206 ratio of Cu(II)-Tilmanocept versus +0 Ctrl from 3 volunteers following exposure to increasing concentrations of Cu(II)-Tilmanocept for 23 hours or 48 hours.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH2CH2O— units in the polyester, regardless of whether ethylene glycol was used to prepare the polyester. Similarly, a sebacic acid residue in a polyester refers to one or more —CO(CH2)8CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A1," "A2," "A3," and "A4" are used herein as generic symbols to represent various specific substituents. These symbols can be any substituent, not limited to those disclosed herein, and when they are defined to be certain substituents in one instance, they can, in another instance, be defined as some other substituents.

"R1," "R2," "R3," "Rn," where n is an integer, as used herein can, independently, possess one or more of the groups listed above. For example, if R1 is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As used herein, the term "pharmaceutically acceptable carrier" or "carrier" refers to sterile aqueous or nonaqueous solutions, colloids, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The term "polarization" is used herein to designate the phenotypic features and the functional features of the macrophages. The phenotype can be defined through the surface markers expressed by the macrophages. The functionality, can be defined for example based on the nature and the quantity of chemokines and/or cytokines expressed, in particular secreted, by the macrophages. Indeed, the macrophages present different phenotypic and functional features depending of their state, either pro-inflammatory M1-type macrophage or anti-inflammatory M2-type macrophage. M2-type macrophages can be characterized by the expression of surface markers such as CD206, CD11b, PD-L1 and CD200R and then secretion of cytokines such as CCL17. M1-type macrophages can be defined by the expression of surface markers such as CD86 and CCR7 and the secretion of cytokines such as IL-6, TNF-a and IL12p40. In the context of the instant disclosure, "repolarize" the induction of a change in phenotype of M1 macrophages population to M1-type macrophages.

As used herein, the term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. In some embodiments, the present methods can be used to treat a subject having an epithelial cancer, e.g., a solid tumor of epithelial origin, e.g., lung, breast, ovarian, prostate, renal, pancreatic, or colon cancer.

As used herein, the term "subject" refers to the target of administration, e.g., an animal. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more cancer disorders prior to the administering step.

As used herein, the term "synergistic" means that the effect achieved with the methods and combinations of this invention is greater than the sum of the effects that result from using the compounds, compositions, treatments and/or methods a pharmaceutically acceptable salt thereof, separately. Advantageously, such synergy provides greater efficacy at the same doses, and/or prevents or delays the build-up of multi-drug resistance.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with cancer" means having been subjected to a physical examination by a person of skill, for example, a physician, and found to have a condition that can be diagnosed or treated by a compound or composition that can reduce tumor size or slow rate of tumor growth. A subject having cancer, tumor, or at least one cancer or tumor cell, may be identified using methods known in the art. For example, the anatomical position, gross size, and/or cellular composition of cancer cells or a tumor may be determined using contrast-enhanced MRI or CT. Additional methods for identifying cancer cells can include, but are not limited to, ultrasound, bone scan, surgical biopsy, and biological markers (e.g., serum protein levels and gene expression profiles). An imaging solution comprising a cell-sensitizing composition of the present invention may be used in combination with MRI or CT, for example, to identify cancer cells.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, administration to specific organs through invasion, intramuscular administration, intratumoral administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Effective dosages may be estimated initially from in vitro assays. For example, an initial dosage for use in animals may be formulated to achieve a circulating blood or serum concentration of active compound that is at or above an IC50 of the particular compound as measured in an in vitro assay. Calculating dosages to achieve such circulating blood or scrum concentrations, taking into account the bioavailability of the particular active agent, is well within the capabilities of skilled artisans. For guidance, the reader is referred to Fingl & Woodbury, "General Principles," In: Goodman and Gilman's The Pharmaceutical Basis of Therapeutics, Chapter 1, pp. 1-46, latest edition, Pergamagon Press, which is hereby incorporated by reference in its entirety, and the references cited therein.

The phrase "anti-cancer composition" can include compositions that exert antineoplastic, chemotherapeutic, antiviral, antimitotic, antitumorgenic, anti-angiogenic, antimetastatic and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agents available in commercial use, in clinical evaluation and in pre-clinical development, which could be included in this application by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

"Tilmanocept" refers to a non-radiolabeled active pharmaceutical ingredient (API) of the LYMPHOSEEK® diagnostic agent. Tilmanocept is a mannosylaminodextran. It has a dextran backbone to which a plurality of amino-terminated leashes (—O(CH$_2$)$_3$S(CH$_2$)$_2$NH$_2$) are attached to the core glucose elements. In addition, mannose moieties are conjugated to amino groups of a number of the leashes, and the chelator diethylenetriamine pentaacetic acid (DTPA) may be conjugated to the amino group of other leashes not containing the mannose. Tilmanocept generally, has a dextran backbone, in which a plurality of the glucose residues comprise an amino-terminated leash:

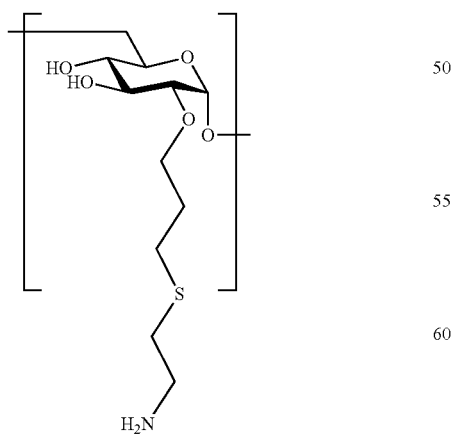

the mannose moieties are conjugated to the amino groups of the leash via an amidine linker:

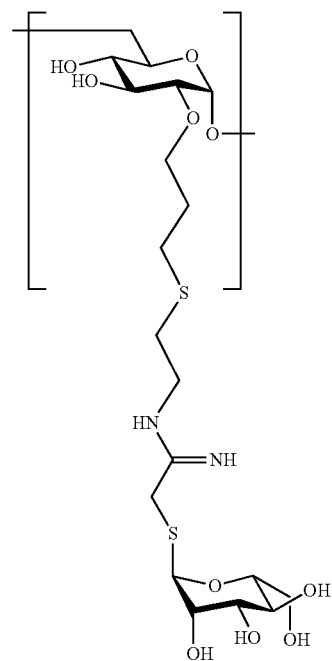

the chelator diethylenetriamine pentaacetic acid (DTPA) is conjugated to the amino groups of the leash via an amide linker:

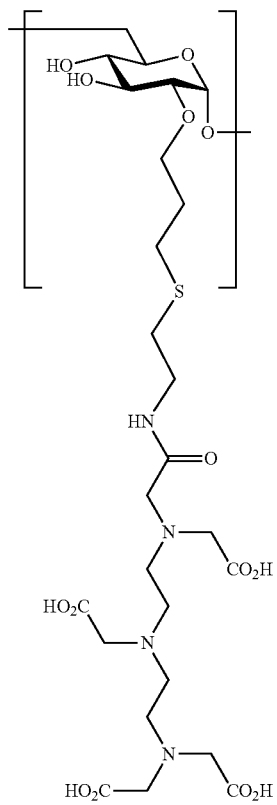

Tilmanocept has the chemical name dextran 3-[(2-aminoethyl)thio]propyl 17-carboxy-10,13,16-tris(carboxymethyl)-8-oxo-4-thia-7,10,13,16-tetraazaheptadec-1-yl 3-[[2-

[[1-imino-2-(D-mannopyranosylthio)ethyl]amino]ethyl]thio]propyl ether complexes, and tilmanocept Tc99m has the following molecular formula: $[C_6H_{10}O_5]_n \cdot (C_{19}H_{28}N_4O_9S^{99m}Tc)_b \cdot (C_{13}H_{24}N_2O_5S_2)_c \cdot (C_5H_{11}NS)_a$ and contains 3-8 conjugated DTPA molecules (b); 12-20 conjugated mannose molecules (c); and 0-17 amine side chains (a) remaining free. Tilmanocept has the following general structure:

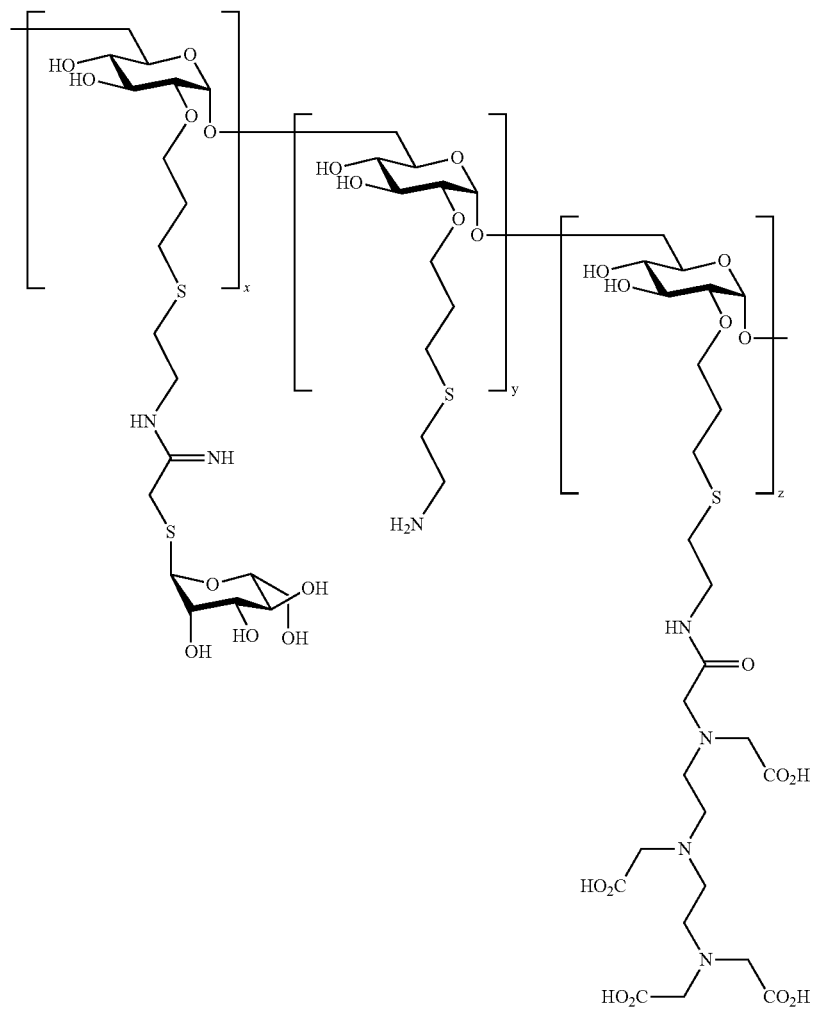

Certain of the glucose moieties may have no attached amino-terminated leash.

The instant disclosure describes compositions and methods with utility for altering or transitioning the phenotype of activated macrophages from being an immunosuppressive phenotype to a proinflammatory phenotype (referred to herein as "repolarizing"). The ability to alter or transition the phenotype of activated macrophages from immunosuppressive to proinflammatory constitutes a therapeutic modality for cancer, various infectious diseases and other medical conditions. The present disclosure further describes a drug delivery vehicle and methods of use that enables the targeted delivery of small molecules and/or metal ions to TAMs with the intent to repolarize the TAMs. TAM targeted delivery provides higher mass doses of the small molecules and ions to TAMs—increasing phenotype altering effects—while limiting potentially toxic exposure to off target cells and tissues. Through the use of the disclosed compositions and methods, M2-like (immunosuppressive) activated macrophages can be induced to switch their phenotype to a M1-like (proinflammatory) activated phenotype by exposure to various small molecules or metal ions.

Compounds

In certain aspects, compounds disclosed herein employ a carrier construct comprising a polymeric (e.g. carbohydrate) backbone having conjugated thereto mannose-binding C-lectin type receptor targeting moieties (e.g. mannose) to deliver one or more active therapeutic agent. Examples of such constructs include mannosylamino dextrans (MAD), which comprise a dextran backbone having mannose molecules conjugated to glucose residues of the backbone and having an active pharmaceutical ingredient conjugated to glucose residues of the backbone. Tilmanocept is a specific example of an MAD. A tilmanocept derivative that is tilmanocept without DTPA conjugated thereto is a further example of an MAD.

In certain implementations, the disclosure provides a compound comprising a dextran-based moiety or backbone having one or more mannose-binding C-type lectin receptor targeting moieties and one or more therapeutic agents attached thereto. The dextran-based moiety generally comprises a dextran backbone similar to that described in U.S.

Pat. No. 6,409,990 (the '990 patent), which is incorporated herein by reference. Thus, the backbone comprises a plurality of glucose moieties (i.e., residues) primarily linked by α-1,6 glycosidic bonds. Other linkages such as α-1,4 and/or α-1,3 bonds may also be present. In some embodiments, not every backbone moiety is substituted. In some embodiments, mannose-binding C-type lectin receptor targeting moieties are attached to between about 10% and about 50% of the glucose residues of the dextran backbone, or between about 20% and about 45% of the glucose residues, or between about 25% and about 40% of the glucose residues. In some embodiments, the dextran-based moiety is about 50-100 kD. The dextran-based moiety may be at least about 50 kD, at least about 60 kD, at least about 70 kD, at least about 80 kD, or at least about 90 kD. The dextran-based moiety may be less than about 100 kD, less than about 90 kD, less than about 80 kD, less than about 70 kD, or less than about 60 kD. Alternatively, in some embodiments, the dextran backbone has a MW of between about 1 and about 50 kDa, while in other embodiments the dextran backbone has a MW of between about 5 and about 25 kDa. In still other embodiments, the dextran backbone has a MW of between about 8 and about 15 kDa, such as about 10 kDa. While in other embodiments the dextran backbone has a MW of between about 1 and about 5 kDa, such as about 2 kDa.

According to further aspects, the mannose-binding C-type lectin receptor targeting moiety is selected from, but not limited to, mannose, fucose, and n-acetylglucosamine. In some embodiments, the targeting moieties are attached to between about 10% and about 50% of the glucose residues of the dextran backbone, or between about 20% and about 45% of the glucose residues, or between about 25% and about 40% of the glucose residues. MWs referenced herein, as well as the number and degree of conjugation of receptor substrates, leashes, and diagnostic/therapeutic moieties attached to the dextran backbone refer to average amounts for a given quantity of carrier molecules, since the synthesis techniques will result in some variability.

According to certain embodiments, the one or more mannose-binding C-type lectin receptor targeting moieties and one or more therapeutic agents are attached to the dextran-based moiety by way of a linker. The linker may be attached at from about 50% to about 100% of the backbone moieties or about 70% to about 90%. The linkers may be the same or different. In some embodiments, the linker is an amino-terminated linker. In some embodiments, the linkers may comprise —O(CH2)3S(CH2)2NH—. In some embodiments, the linker may be a chain of from 1 to 20 member atoms selected from carbon, oxygen, sulfur, nitrogen and phosphorus. The linker may be a straight chain or branched. The linker may also be substituted with one or more substituents including, but not limited to, halo groups, perfluoroalkyl groups, perfluoroalkoxy groups, alkyl groups, such C1-4 alkyl, alkenyl groups, such as C1-4 alkenyl, alkynyl groups, such as C1-4 alkynyl, hydroxy groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, —NH—NH2; =N—H; =N-alkyl; —SH; —S-alkyl; —NH—C(O)—; —NH—C (=N)— and the like. As would be apparent to one skilled in the art, other suitable linkers are possible.

In some embodiments, the one or more therapeutic agent is attached via a biodegradable linker. In some embodiments, the biodegradable linker comprises a pH sensitive moiety, such as a hydrazone. At lower (more acidic) pH, hydrazone linkers spontaneously hydrolyze at increasing rates as pH decreases. When a mannosylated dextran binds to CD206, it is internalized to endosomes which become increasingly acidified over time, thereby releasing the therapeutic agent payloads intracellularly.

In certain embodiments, the therapeutic agent is capable repolarizing M2-macrophages to M1 macrophages when attached to the MAD carriers disclosed herein. In further embodiments, the therapeutic agent is capable of inducing T-Cell activation.

According to further embodiments, the therapeutic agent is a cytotoxic agent. In still further embodiments, the therapeutic agent is an anti-cancer agent.

In certain alternative embodiments, the compound is any of the a carrier construct comprising a polymeric (e.g. carbohydrate) backbone having conjugated thereto mannose-binding C-lectin type receptor targeting moieties disclosed herein, but without a therapeutic moiety/agent conjugated thereto. In exemplary implementations of these embodiments, such compounds are administered in conjunction with one or more therapy or treatment, as described in greater detail below.

According to certain further embodiments, the therapeutic agent is selected from: paclitaxel, gemcitabine, lapatinib, and doxorubicin. In further embodiments, the therapeutic agent is doxorubicin. In certain aspects, administration of the composition to the subject has reduced toxicity relative to an equivalent dose of the therapeutic agent not conjugated to the composition.

According to certain embodiments the therapeutic agent is a bisphosphonate. In exemplary implementations of these embodiments, the bisphosphonate is zoledronic acid.

In certain aspects, the therapeutic agent is a metal ion. In certain exemplary embodiments, metals such as arsenic, antimony silver, cadmium, gallium or gadolinium are the therapeutic agent.

In exemplary embodiments, the metal ion is Cu(II). In exemplary aspects of these embodiments, the Cu(II) ion is bound to a chelator (as described further below) on one or more leashes. In certain aspects, the therapeutic agent is comprised of one or more Cu(II) ions per molecule of compound. In further embodiments, the therapeutic agent is comprised of from lCu(II) ion to a number of Cu(II) ions equal to the number of chelator moieties. In yet further embodiments, the number of Cu(II) ions is from 1 to 12 Cu(II) ions. In even further embodiments, the number of Cu(II) ions is from 3 to 8 Cu(II) ions In still further embodiments, the therapeutic agent is comprised of about 4 Cu(II) ions.

In certain aspects, a chelating agent may be attached to or incorporated into a disclosed compound, and used to chelate a therapeutic agent, such as Cu(II). Exemplary chelators include but are not limited to DTPA (such as Mx-DTPA), DOTA, TETA, NETA or NOTA. According to certain exemplary implementations, the chelator is DOTA.

Further disclosed herein is compound for repolarizing a TAM from M2 to M1 comprising a compound of Formula (I):

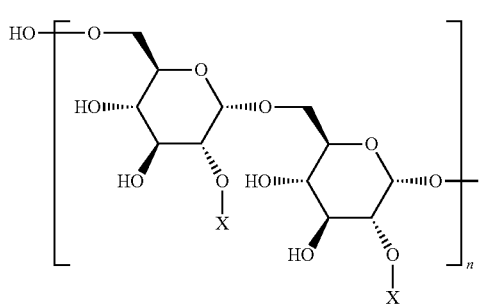

(I)

wherein
each X is independently H, L1-A, or L2-R;
each L1 and L2 are independently linkers;
each A independently comprises a therapeutic agent or H;
each R independently comprises a mannose-binding C-type lectin receptor targeting moiety or H; and n is an integer greater than zero; and
wherein at least one R comprises a mannose-binding C-type lectin receptor targeting moiety selected from the group consisting of mannose, fucose, and n-acetylglucosamine and at least one A comprises a therapeutic agent, wherein the therapeutic agent comprises a chelator and at least one Cu(II) ion.

In certain implementations, at least one L1 comprises —(CH2)pS(CH2)q-NH—, wherein p and q are integers from 0 to 5.

In further aspects, at least one L2 is a C2-12 hydrocarbon chain optionally interrupted by up to three heteroatoms selected from the group consisting of O, S and N.

In yet further aspects, at least one L2 comprises —(CH2)pS(CH2)q-NH—, wherein p and q independently are integers from 0 to 5.

Further disclosed herein is a compound for repolarizing a TAM from M2 to M1 comprising a compound of Formula (I):

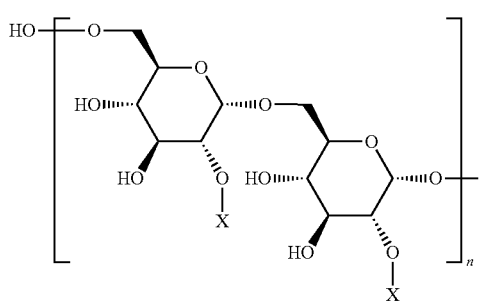

(I)

wherein each X is independently H, L1-A, or L2-R;
each L1 and L2 are independently linkers;
each A independently comprises a therapeutic agent or H;
each R independently comprises a mannose-binding C-type lectin receptor targeting moiety or H;
and n is an integer greater than zero; and
wherein at least one R comprises a mannose-binding C-type lectin receptor targeting moiety selected from the group consisting of mannose, fucose, and n-acetylglucosamine and at least one A comprises a therapeutic agent, wherein the therapeutic agent comprises doxorubicin.

In certain implementations, each L1 is a hydrazone linker.

According to further implementations, the ratio of mannose-binding C-type lectin receptor targeting moieties to doxorubicin moieties is about 18.5 to about 1.5. In still further implementations, the dextran backbone is about 10 kD.

In further embodiments, the disclosed composition is of formula (II)

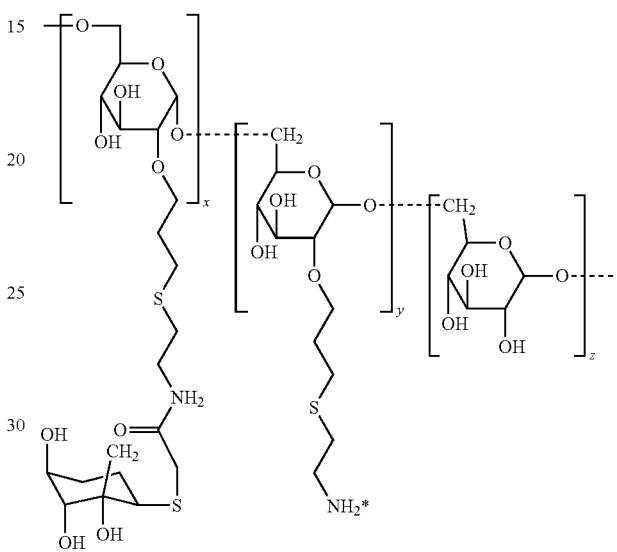

(II)

wherein the * indicates the point at which the therapeutic agent is attached. In certain embodiments, the therapeutic agent is attached via a linker.

According to certain embodiments, the disclosed compounds can include a pharmaceutically acceptable carrier and a compound or a pharmaceutically acceptable salt of the compounds disclosed herein. The disclosed compounds, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques Further disclosed herein are methods of using the disclosed compounds. In certain embodiments, is a method for repolarizing a tumor associated macrophage (TAM) from M2 to M1 comprising administering to a subject in need thereof an effective amount of a compound disclosed herein.

In certain aspects, the compound is administered in a therapeutically effective amount. In further aspects, the compound is administered in prophylactically effective amount.

In yet further aspects, the method further comprises administering the compound intravenously, intraperitoneally, intramuscularly, orally, subcutaneously intraocularly, intra-tumor injection or transdermally or delivered directly to tumor organ by invasive techniques.

In still further aspects, the method further comprises administering the composition in conjunction with at least one other treatment or therapy. In even further aspects, the other treatment or therapy comprises co-administering an anti-cancer agent. In further aspects, the other treatment or therapy is chemotherapy. In certain aspects, the compound is administered alone or in combination with other chemical based therapeutics or with radiation therapy or thermal therapy or physical therapy or dietary therapy.

According to further embodiments, the at least one other treatment or therapy is an immunotherapy, such as, the administration of an immunomodulatory agent. According to certain implementations, the at least one other treatment or therapy is anti-CTLA4 immunotherapy. In certain implementations, the immunomodulatory agent is an immunostimulator. In some embodiments, the immunomodulatory agent is a glucocorticoid, hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a cytostatic agent, an alkylating agent, nitrogen mustard (cyclophosphamide), nitrosourea, a platinum compound, an antimetabolite, a purine analog, azathioprine, mercaptopurine, mycophenolic acid, a pyrimidine synthesis inhibitor, leflunomide, teriflunomide, a folic acid analog, methotrexate, a cytotoxic antibiotic, dactinomycin, anthracyclines, mitomycin C, bleomycin, mithramycin, an antibody or fusion thereof, anti-thymocyte globulin, anti-lymphocyte globulin, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CD11a antibody, efalizumab, an anti-CD18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, ipilimumab, tremelimumab, an anti-eotaxin 1 antibody, bertilimumab, an anti-α4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an immunophilin modulating agent, rapamycin, a calcincurin inhibitor, tacrolimus, ciclosporin (cyclosporin), pimecrolimus, abetimus, gusperimus, ridaforolimus, everolimus, temsirolimus, zotarolimus, a TNF inhibitor, infliximab, adalimumab, certolizumab pegol, golimumab, etanercept, thalidomide, lenalidomide, pentoxifylline, bupropion, curcumin, catechin, an IL-1 receptor antagonist, anakinra, an anti-IL-5 antibody, mepolizumab, an IgE inhibitor, omalizumab, talizumab, an IL12 inhibitor, an IL23 inhibitor, ustekinumab, an opiod, an IMPDH inhibitor, mycophenolic acid, myriocin, fingolimod, an NF-κB inhibitor, raloxifene, drotrecogin alfa, denosumab, an NF-κB signaling cascade inhibitor, disulfiram, olmesartan, dithiocarbamate, a proteasome inhibitor, bortezomib, MG132, Pro1, NPI-0052, curcumin, genistein, resveratrol, parthenolide, thalidomide, lenalidomide, flavopiridol, non-steroidal anti-inflammatory drugs (NSAIDs), arsenic trioxide, dehydroxymethylepoxyquinomycin (DHMEQ), 13C(indole-3-carbinol)/DIM(di-indolmethane) (I3C/DIM), Bay 11-7082, luteolin, cell permeable peptide SN-50, IκBα-super repressor overexpression, NFκB decoy oligodeoxynucleotide (ODN), or a derivative or analog of any thereof.

In exemplary implementations, the combined administration of the compound and the at least one treatment or therapy is synergistically effective relative to administration of either alone.

According to certain embodiments, administration of the compounds disclosed herein in conjunction with another therapy or treatment is associated with reduced toxicity compared to administration of the other therapy or treatment alone. In further embodiments, the co-administration of the instantly disclosed compounds and other therapy or treatment produce a synergic effect. In yet further embodiments, the co-administration of the instantly disclosed compounds and provides for lower effective dose of the other therapy or treatment.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first line therapy. In some embodiments, the method is used as a second line therapy.

According to certain aspects, the subject has been diagnosed with melanoma, breast cancer, lung carcinoma, pancreatic carcinoma, renal carcinoma, ovarian, prostate or cervical carcinoma, glioblastoma, or colorectal carcinoma, cerebrospinal tumor, head and neck cancer, thymoma, mesothelioma, esophageal cancer, stomach cancer, liver cancer, pancreatic cancer, bile duct cancer, bladder cancer, testicular cancer, germ cell tumor, ovarian cancer, uterine cervical cancer, endometrial cancer, lymphoma, acute leukemia, chronic leukemia, multiple myeloma, sarcoma, or any combination thereof.

In certain aspects, the method further comprises administering the composition as a bolus and/or at regular intervals. In certain aspects, the disclosed method further comprises administering the composition intravenously, intraperitoneally, intramuscularly, orally, subcutaneously, intra-tumorally or transdermally.

According to certain further embodiments, the method further comprises diagnosing the subject with cancer. In further aspects, the subject is diagnosed with cancer prior to administration of the composition. According to still further aspects, the method further comprises evaluating the efficacy of the composition. In yet further aspects, evaluating the efficacy of the composition comprises measuring tumor size prior to administering the composition and measuring tumor size after administering the compound. In even further aspects, evaluating the efficacy of the composition occurs at regular intervals. According to certain aspects, the disclosed method further comprises optionally adjusting at least one aspect of method. In yet further aspects, adjusting at least one aspect of method comprises changing the dose of the composition, the frequency of administration of the composition, or the route of administration of the compound.

According to certain alternative embodiments, the subject has been diagnosed with a disease associated with elevated levels of CD206+ macrophages and/or MDSC. Such diseases or conditions include, but are not limited to: acquired immune deficiency syndrome (AIDS), acute disseminated encephalomyelitis (ADEM), Addison's disease, agammaglobulinemia, allergic diseases, alopecia areata, Alzheimer's disease, amyotrophic lateral sclerosis, ankylosing spondylitis, antiphospholipid syndrome, antisynthetase syndrome, arterial plaque disorder, asthma, atherosclerosis, atopic allergy, atopic dermatitis, autoimmune aplastic anemia, autoimmune cardiomyopathy, autoimmune enteropathy, autoimmune hemolytic anemia, autoimmune hepatitis, autoimmune hypothyroidism, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Balo disease/Balo concentric sclerosis, Behcet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, chronic venous stasis ulcers, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's Syndrome, cutaneous leukocytoclastic angiitis, Dego's disease, Dercum's disease, dermatitis herpetiformis, dermatomyositis, Diabetes mellitus type I, Diabetes mellitus type II diffuse cutaneous systemic sclerosis, Dressler's syndrome, drug-induced lupus, discoid lupus erythematosus, eczema, emphysema, endometriosis, enthesitis-related arthritis, eosinophilic fasciitis, eosinophilic gastroenteritis, eosinophilic pneumonia, epidermolysis bullosa acquisita, erythema nodosum, erythroblastosis fetalis, essential mixed cryoglobulinemia, Evan's syndrome, fibrodysplasia ossificans progressive, fibrosing alveolitis (or idiopathic pulmonary fibrosis), gastritis, gastrointestinal pemphigoid, Gaucher's disease, glomerulonephritis, Goodpasture's syndrome, Graves' disease, Guillain-Barré syndrome (GBS), Hashimoto's encephalopathy, Hashimoto's thyroiditis, heart disease, Henoch-Schonlein purpura, herpes gestationis (aka gestational pemphigoid), hidradenitis suppurativa, HIV infection, Hughes-Stovin syndrome, hypogammaglobulinemia, infectious diseases (including bacterial infectious diseases), idiopathic inflammatory demyelinating diseases, idiopathic pulmonary fibrosis, idiopathic thrombocytopenic purpura, IgA nephropathy, inclusion body myositis, inflammatory arthritis, inflammatory bowel disease, inflammatory dementia, interstitial cystitis, interstitial pneumonitis, juvenile idiopathic arthritis (aka juvenile rheumatoid arthritis), Kawasaki's disease, Lambert-Eaton myasthenic syndrome, leukocytoclastic vasculitis, lichen planus, lichen sclerosus, linear IgA disease (LAD), lupoid hepatitis (aka autoimmune hepatitis), lupus erythematosus, lymphomatoid granulomatosis, Majeed syndrome, malignancies including cancers (e.g., sarcoma, Kaposi's sarcoma, lymphoma, leukemia, carcinoma and melanoma), Meniere's disease, microscopic polyangiitis, Miller-Fisher syndrome, mixed connective tissue disease, morphea, Mucha-Habermann disease (aka Pityriasis lichenoides et varioliformis acuta), multiple sclerosis, myasthenia gravis, myositis, narcolepsy, neuromyelitis optica (aka Devic's disease), neuromyotonia, ocular cicatricial pemphigoid, opsoclonus myoclonus syndrome, Ord's thyroiditis, palindromic rheumatism, PANDAS (pediatric autoimmune neuropsychiatric disorders associated with streptococcus), paraneoplastic cerebellar degeneration, Parkinsonian disorders, paroxysmal nocturnal hemoglobinuria (PNH), Parry Romberg syndrome, Parsonage-Turner syndrome, pars planitis, pemphigus vulgaris, peripheral artery disease, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restenosis, restless leg syndrome, retroperitoneal fibrosis, rheumatoid arthritis, rheumatic fever, sarcoidosis, schizophrenia, Schmidt syndrome, Schnitzler syndrome, scleritis, scleroderma, sepsis, serum Sickness, Sjogren's syndrome, spondyloarthropathy, Still's disease (adult onset), stiff person syndrome, stroke, subacute bacterial endocarditis (SBE), Susac's syndrome, Sweet's syndrome, Sydenham chorea, sympathetic ophthalmia, systemic lupus erythematosus, Takayasu's arteritis, temporal arteritis (aka "giant cell arteritis"), thrombocytopenia, Tolosa-Hunt syndrome,) transplant (e.g., heart/lung transplants) rejection reactions, transverse myelitis, tuberculosis, ulcerative colitis, undifferentiated connective tissue disease, undifferentiated spondyloarthropathy, urticarial vasculitis, vasculitis, vitiligo, and Wegener's granulomatosis.

EXAMPLES

The following examples are put forth so as to provide those of ordinary skill in the art with a complete disclosure and description of certain examples of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Example 1

Copper (II) [Cu(II)] tilmanocept repolarizes M2-like macrophages towards a M1-like phenotype CD206 is expressed at a higher level on most M2-like macrophages, including M2-like TAMs, than it is on M1-like macrophages. Thus, tilmanocept will localize to M2-like TAMs. In a first experiment, tilmanocept was loaded with Cu[II] ions at a rate of approximately 3.9 copper ions per tilmanocept molecule via chelation to tilmanocept's DTPA moieties. Human peripheral blood monocytes from three human volunteers were induced to adopt a M2-like phenotype by placing them in RPMI-1640 medium supplemented with fetal bovine serum to a final concentration of 10% plus 2.0 g/L glucose, 0.3 g/L L-glutamine, 2.0 g/L NaHCO3, and 1 mL sodium pyruvate (11 g/L). To this culture medium granulocyte-macrophage colony-stimulating factor (GM-CSF) was also added to a concentration of 50 ng/ml. Flasks containing monocytes in this culture medium were incubated for three days to induce differentiation to CD206 expressing macrophages with a M2 phenotype. These cells also express the myeloid cell surface marker CD14.

The CD14+ CD206+ M2 macrophages were then incubated in the same culture medium with varying concentration of Cu(II)-tilmanocept: 0, 1, 2, 4, 8, 16 (ug/ml). These concentrations of Cu(II)-tilmanocept are equal to approximately 0, 50, 100, 200, 400, 800 nM. Cultures were incubated for either 23 or 48 hours after which they were evaluated by flow cytology for expression of CD206 and cell surface markers for macrophages with a M1-like phenotype: CD80 and CD86.
Treatment with Cu(II)-Tilmanocept Caused CD206 Expression on Macrophages to Decrease.

FIG. 1 shows that While there were differences between macrophages derived from the three volunteer donors relative to the geometric mean fluorescence of CD206+ macrophages in the untreated control macrophages, Cu(II)-tilmanocept exposure decreased the amount of CD206 immunofluorescence from approximately 40-60+%, indicating a transition of these macrophages from a M2-like phenotype to a more M1-like phenotype (FIG. 1). It is noted that the large majority of the observed change in CD206 expression occurred at Cu(II)-tilmanocept concentrations of 1.0 μg/ml or 2.0 μg/ml (50 nm or 100 nm) and that most of the change occurred within 23 hours as shown in FIG. 2. FIG. 2. The ratio of CD206 expression compared to untreated controls observed on macrophages treated with increasing concentrations of Cu(II)-tilmanocept for either 23 or 48 hours. Macrophages from three donors were evaluated. Red; Volunteer donor A (23 hours), Blue and Green; Volunteer donors B and C (48 hours)At these lower concentrations of Cu(II)-tilmanocept (50 nm and 100nm), Cu(II)-tilmanocept did not significantly increase the rate of cell death over what was observed on the untreated control macrophages that were incubated in the same medium for the same amounts of time (data not shown).

Figure 3:
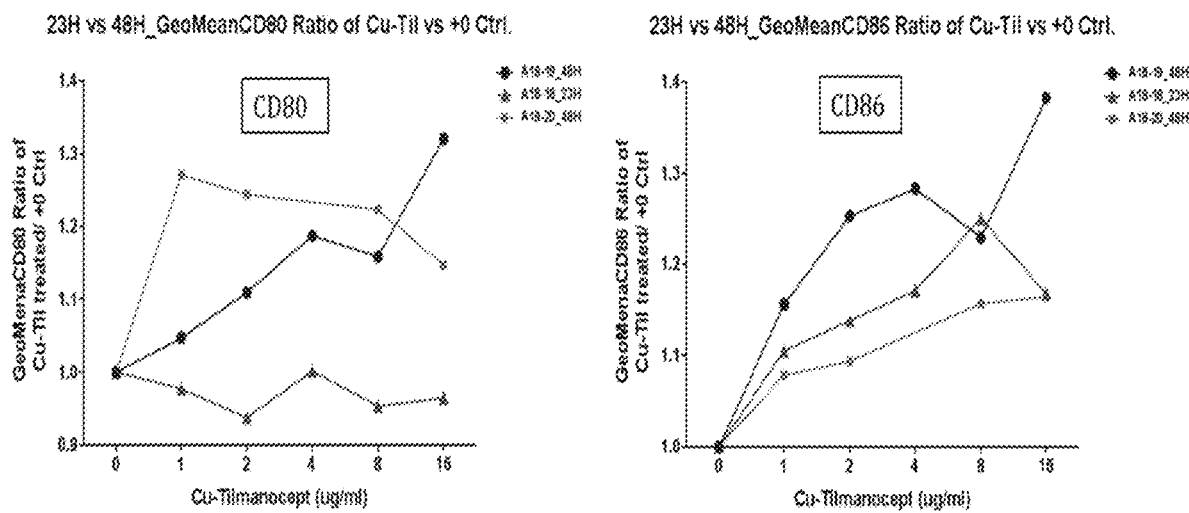
FIG. 3 shows changes in expression of CD80 and CD86 by M2 macrophages upon increasing exposure to Cu(II)-tilmanocept for either 23 hours or 48 hours

CD80 and CD86 are cell surface markers that can be expressed by a variety of immune cells. M1-like activated macrophages express higher levels of CD80 and CD86 than do M2-like macrophages. CD80 and CD86 form a receptor complex that binds to CD28 expressed on T-cell, resulting in T-cell activation. Expression of both CD80 and CD86 are increased by exposure to Cu(II)-tilmanocept and especially after 48 hours of exposure (FIG. 3).

Although the trend for increasing expression of CD80 and CD86 was not as strong as was observed for decreasing expression of CD206, a significant portion of the increased expression was observed at a relatively low concentration of 2.0 μg/ml (100 nm) of Cu(II)-tilmanocept.

Figure 4:
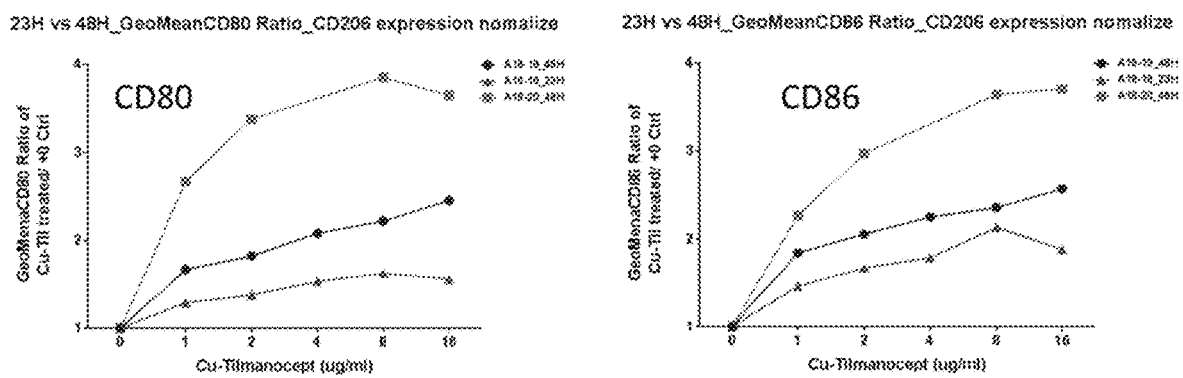
FIG. 4 shows changes in expression of CD80 and CD86 normalized to changes in CD206 expression in CD206+ M2 macrophages treated with Cu(II)-tilmanocept at increasing concentrations for either 23 or 48 hours.

The repolarization of M2-like macrophages to M1-like macrophages is manifested as a decrease in expression of M2 markers and an increase in expression of M1 markers. Therefore, a measure of the efficiency of repolarization by Cu(II)-tilmanocept can be expressed by the change in CD80 and CD86 expression on Cu(II)-tilmanocept treated macrophages relative to the untreated controls (FIG. 3) normalized to CD206 expression changes on similarly treated macrophages (FIG. 2). The results of this analysis are shown in FIG. 4. The results of these CD206 expression normalized analyses indicate that Cu(II)-tilmanocept causes a repolarization of M2-like macrophages to a more M1-like macrophage phenotype in a concentration and time dependent manner.

Example 2

A Mannosylated Dextran Construct Carrying a Doxorubicin Payload Repolarizes M2-Like Macrophages Towards a M1-Like Phenotype The potential therapeutic strategy described in Example 1 is not limited to delivering metal ions to CD206 expressing macrophages and can be employed to deliver a wide variety of small molecule payloads to CD206+ macrophages to repolarize them or alter their phenotype. In a second set of experiments, a mannosylated dextran carrying a payload of the cytotoxic agent, doxorubicin, was synthesized and evaluated. This construct, like tilmanocept in Example 1, was synthesized on a 10 kD dextran backbone to which were conjugated mannose moieties via amine terminated leashes. Unoccupied amine terminated leashes were conjugated to hydrazone linkers to which doxorubicin was then added. Hydrazone linkers are known to release their payloads more rapidly at lower pH than at neutral pH. When CD206 binds to a ligand, such as a mannosylated dextran, it is internalized to endosomes by receptor mediated endocytosis. These endosomes undergo acidification that accelerates the release of the drug payload from the hydrazone linkers. The construct that was evaluated in the experiments described in this example carried an average of 18.5 mannose moieties and 1.5 doxorubicin moieties per 10 kD dextran backbone and for convenience is referred to as MT1001.8 in this discussion.

As with Cu(II)-tilmanocept, MT1001.8 was evaluated using macrophages differentiated from human peripheral blood monocytes cultured in supplemented RPMI-1640 medium to which GM-CSF was added. The resulting macrophages were then exposed for 23 hours to MT1001.8 at different concentrations ranging from 0 (controls) to 6.68 μM. Free doxorubicin and the mannosylated dextran construct without the doxorubicin payload were also evaluated as controls. After the 23-hour exposure to the drug construct, the drug containing media were removed and replaced with fresh supplemented RPMI-1640 with GM-CSF and incubated for an additional 72 hours. This final 72-hour incubation in fresh medium was to permit the macrophages to recover from the drug treatment and to manifest any phenotype changes that might have been induced by exposure to the drug construct. All experiments were replicated 5-8 times with peripheral blood monocytes obtained from 5 separate donors. After the last 72-hour incubation, the media were collected and analyzed for their concentrations of various cytokines. The cells were collected and evaluated by flow cytometry for their expression various cell surface markers of differentiation (CD206, CD64, CD163, CD80 and CD86), for dose dependent uptake of doxorubicin, and for cell death.

Similar to what was observed in Example 1, the different human donors provided differentiated macrophages that varied in the magnitude of their responses to MT1001.8. However, all donors' macrophages showed dose dependent responses that were in the same directions. For example, CD86 expression rose in all macrophage cultures exposed to MT1001.8, but the maximum response varied between 2.5 fold to 3.2 fold increased expression at the highest MT1001.8 concentration. For simplicity and clarity, this data is shown as the change in expression relative to the maximum and minimum levels observed in each experiment and displayed as a percent of the maximum change. The results from the free doxorubicin control are not shown because free doxorubicin resulted in high levels of cell death at all concentrations tested. MT1001.8 had markedly less toxicity to macrophages with high cell viability at the end of the 72-hour post-drug exposure incubation even at the highest concentrations. Similarly, the results from the mannosylated dextran without doxorubicin are not shown because except for two examples discussed in a following paragraph, this construct did not alter the expression of the markers examined in this study. Also not shown are results demonstrating that MT1001.8 is taken up by CD206+ macrophages in a dose dependent manner and at rates ≈25× higher than was observed for non-specific binding to lymphocytes, which do not express CD206.

Figure 5:
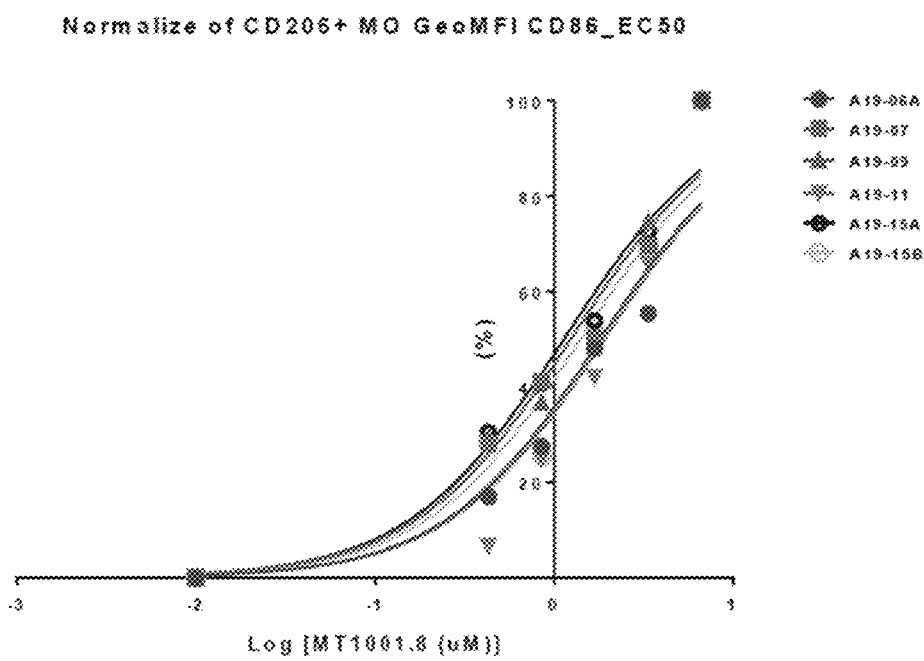
FIG. 5 shows normalized MO CD86 expression data of 6 experiments from 4 donors.
Figure 6:
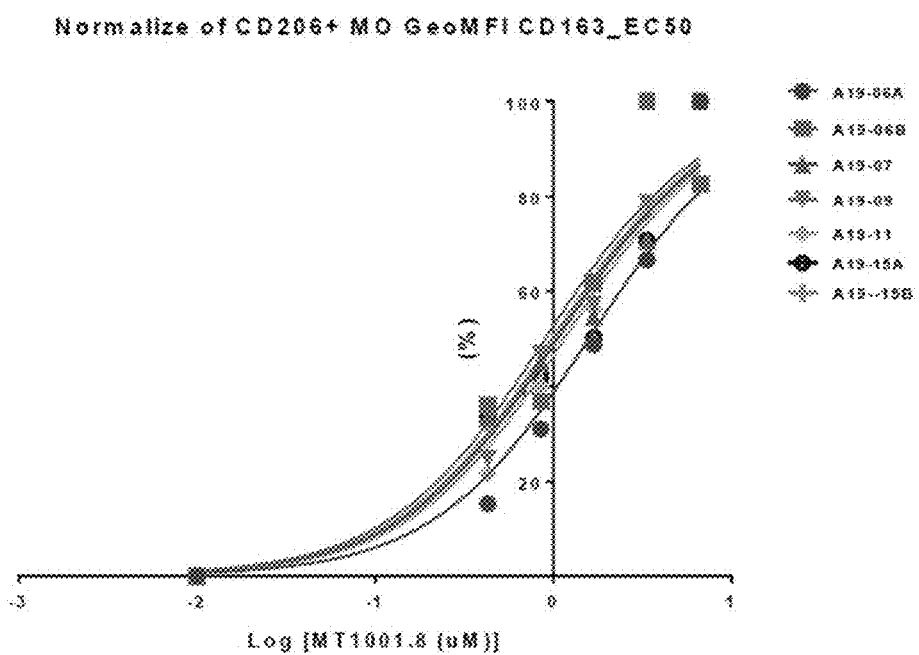
FIG. 6 shows normalized MO CD163 expression data of 7 experiments from 4 donors.
Figure 7:
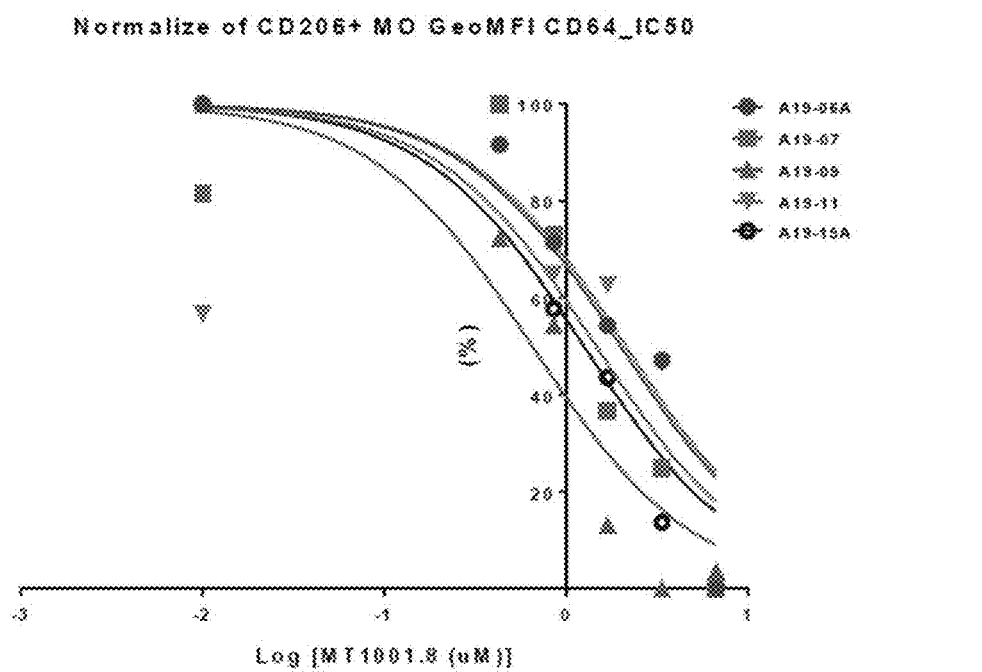
FIG. 7 shows normalized MO CD64 expression data of 5 experiments from 4 donors.
Figure 8:
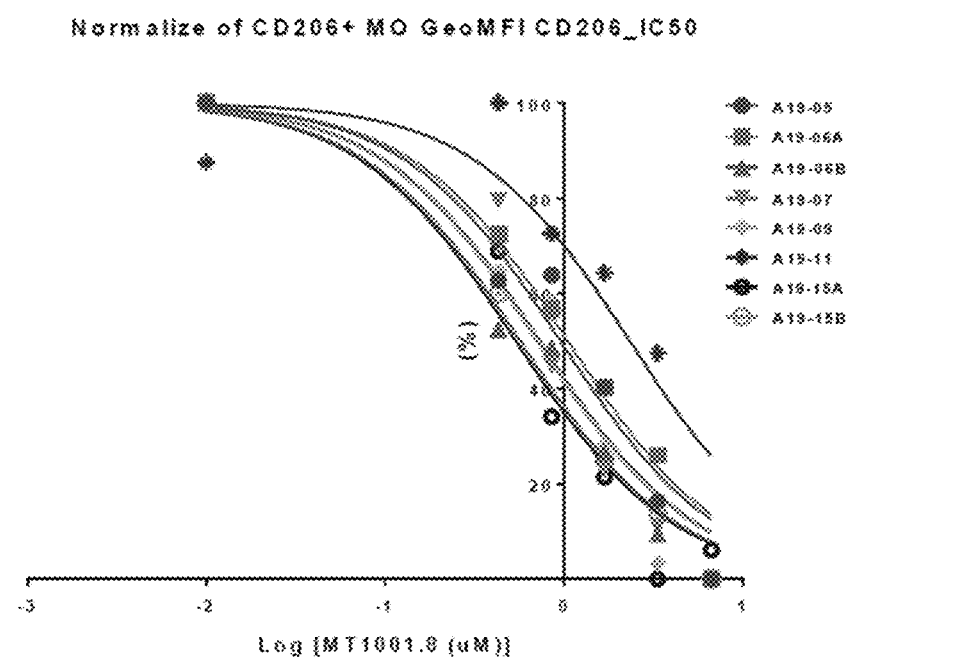
FIG. 8 shows normalized MO CD206 regulation data of 8 experiments from 5 donors.

Two cell surface differentiation markers, CD86 and CD163, showed dose dependent, reproducible, and significant increases in expression upon exposure to MT1001.8. At the highest dose tested (6.68 µM), CD86 and CD163 increased their levels of expression by approximately 2.9 and 2.5-fold respectively across all experiments and macrophages cultures derived from all human donors. These results are summarized in FIGS. 5 and 6 which show the percent of each donor's macrophages maximum change observed at each dose of MT1001.8. The dose response curves displayed in these figures are highly similar for each experiment and show a nearly linear response relative to the log10 of the dose exposure over the range of MT1001.8 concentrations evaluated. As shown in FIGS. 5 and 6, some donors' macrophages were evaluated twice each. The variance between the separate evaluations of macrophages from the same donors suggests that the inter-test variation may explain a large portion of the variance observed between donors, further indicating that the macrophage dose response is robust and reproducible, and highly similar between macrophages obtained from different donors. In contrast to CD86 and CD163, CD64 demonstrated a dose dependent (approximately 40%) decrease in expression upon exposure to MT1001.8 (FIG. 7).

In an unexpected result, the drug free mannosylated dextran without drug payload was observed to alter the expression of two cells surface markers of differentiation, CD206 and CD80. The level of expression of CD80 was increased in expression by about 60% at the highest concentrations of either the drug free mannosylated dextran or MT1001.8, indicating that it was the mannosylated dextran and not the doxorubicin payload of MT1001.8 that was responsible for the change in CD80 expression. It is important to note that the magnitude of the increased expression of CD80 was much less than the magnitude of the increase in impression of CD86 observed upon exposure to MT1001.8; however, it is possibly significant that CD80 and CD86 both bind CD28 and CTLA4. When bound to CD28, they activate pro-inflammatory responses in T-cell. When bound to their competing ligand, CTLA4, T-cell activation is impaired. CD206 expression was also altered by exposure to either the drug free mannosylated dextran or MT1001.8; however, unlike CD80, CD206 expression decreased between 40-50% at the highest concentration of either construct. This effect is unlikely to be the simply result of ligand binding which could reduce the amount of CD206 receptor displayed on the cell surface due to internalization of receptor-ligand complexes because the 72 hour incubation following removal of the drug containing media would have allowed time for the replacement or recycling of CD206 receptors to the surface. This suggests that the reduced expression of CD206 is a change in phenotype and not a transient consequence of receptor binding and internalization. It is also noteworthy that, as with Example 1, 50% of the maximum responses for al 5 surface markers were achieved at concentrations of MT1001.8 or as appropriate the drug free mannosylated dextran at concentrations of between 1 and 2 µM.

At the end of the final 72-hour incubation, the media were collected and evaluated for their concentrations of various cytokines to identify cytokines that were increased in expression as a result of exposure to MT1001.8. There was considerable variance between the base line (no drug —saline control) level of cytokine expression in the macrophage cultures derived from different donors. Therefore, the data were analyzed as the ratio of the cytokine concentration in the drug treated cultures relative to the observed concentration in the donor specific drug free control (saline). Increased concentrations were observed at the higher MT1001.8 treatment concentrations for a portion of the evaluated cytokines as indicated by the mean ratio observed in the MT1001.8 macrophage cultures being more than one standard deviation above 1.0, which is the ratio expected if no change in cytokine expression had occurred. Interferon gamma (IFN-g), Interleukin 2b (IL2b), IL12p70, Tumor Necrosis Factor alpha (TNFa), IL8, and IL10 were all observed to have increased expression levels by this criterion, IL6 also had an elevated level of expression but because of high variance in the data, did not exceed the one standard deviation threshold. Media concentrations of IL4, IL5, and IL7 were not observed to have increased.

All of the cytokines for which increased expression levels were observed, except IL10, are pro-inflammatory and would be expected to promote proinflammatory activation of a wide variety of immune cell types including lymphocytes. The observed changes in cell surface markers of differentiation are also indicative of a change in macrophage gene expression towards a more proinflammatory pattern, especially the increased expression of CD86, and CD80, and the decreased expression of CD206. The increased expression of CD163 is interesting in the context of a recent publication (62) demonstrating the tumor associated macrophages (TAMs) with increased expression of CD163 and decreased expression of CD206 were associated with better gastric cancer patient outcomes. Taken together, the changes in expression of both cell surface markers and cytokines indicate that macrophages treated with MT1001.8 are altering their global phenotypes to become more M1-like and proinflammatory. The observed lower expression of CD64 and the increased expression of IL10 are not entirely consistent with a proinflammatory phenotype, but the large number of other genes with altered expression indicate a much more proinflammatory phenotype repolarization being adopted by macrophages treated with MT1001.8.

The increased expression of CD80 and CD86 coupled with the increased expression of proinflammatory cytokines suggests that MT1001.8 or other similar mannosylated dextran constructs carrying doxorubicin payloads may have efficacy as an anti-cancer immunotherapy and perhaps especially in combination with other cancer therapies. Such combination therapy could include radiotherapies, other cytotoxic agents besides doxorubicin, and perhaps especially, other cancer immunotherapies designed to activate lymphocytes. Anti-CTLA4 antibodies are a regulatorily approved anti-cancer immunotherapy that is designed to activate T-cell lymphocytes. Because of the interactions between CD80 and CD86, and CTLA4 and CD28, it was hypothesized that MT1001.8 could improve the efficacy of anti-CTLA4 immunotherapy. To test this hypothesis, an experiment was performed using the 4T1 syngeneic breast cancer model in Balb/c mice. The 4T1 tumor model is largely resistant to therapy with anti-CTLA4, and it was hypothesized that MT1001.8 could rescue treatment efficacy for this immunotherapy. 4T1 cells were implanted into mice and allowed to form approximately 50mm$^3$ tumors. Six treatment groups were selected: saline control, drug free mannosylated dextran control (vehicle), MT1001.8, free doxorubicin, anti-CTLA4 antibodies, or a combination of anti-CTLA4 and MT1001.8. Animals received tail vein injections of 500 µg of MT1001.8, the vehicle control, saline control, or free doxorubicin (equimolar to MT1001.8) every two days. The anti-CTLA4 antibody was administered at a dose of 500 µg as an intraperitoneal (IP) injection twice weekly. The experimental treatments were conducted for 13 days. The growth of the 4T1 tumors for each treatment is shown in FIG. 9.

Figure 9:
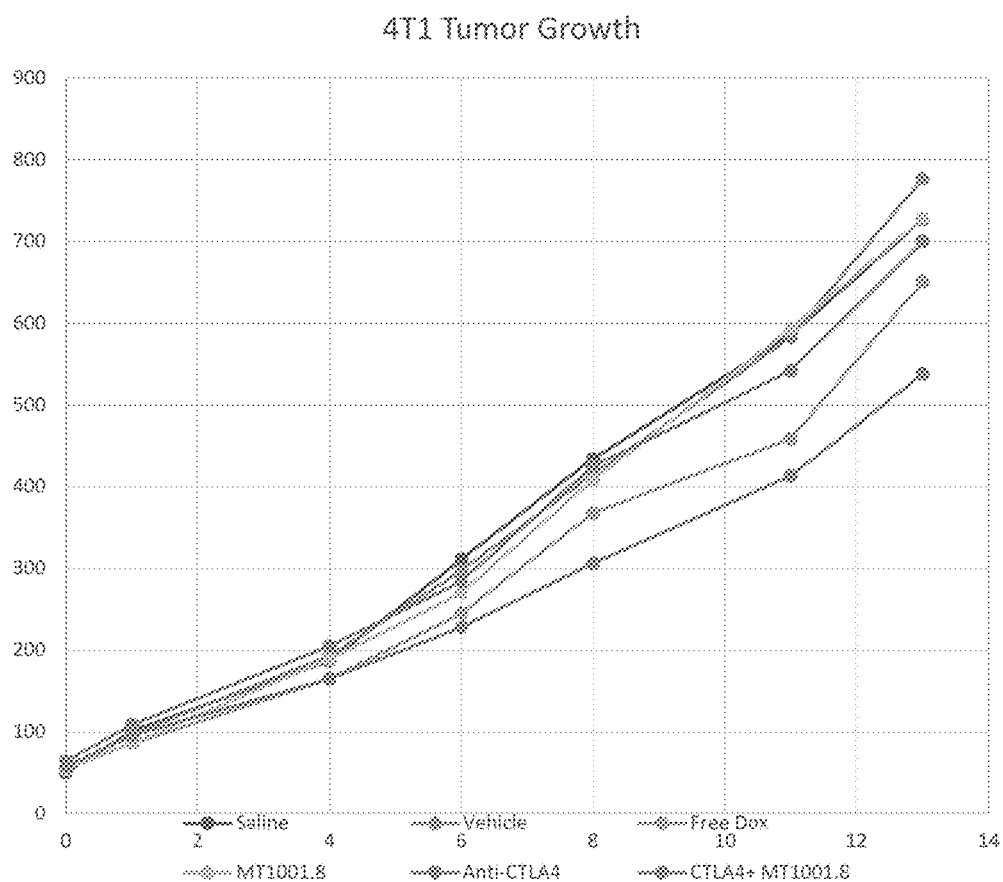
FIG. 9 shows 4TI tumor growth for 6 treatments.

As shown in FIG. 9, None of the treatment groups except for the combination therapy of anti-CTLA4+MT1001.8 had mean tumor volumes that were significantly different from those of either the saline or vehicle control groups. Compared to the vehicle control, the group treated with anti-CTLA4+MT1001.8 had mean tumor volumes that were 69% that of the vehicle control at the end of the experiment. In a 2-tailed T test, this result was significant at a p=0.02, demonstrating that MT1001.8 was able to partially rescue of the efficacy of anti-CTLA therapy in this typically refractile tumor model. This cooperative effect between anti-CTLA4 and MT1001.8 is expected to be widely applicable to other cancer therapies besides anti-CTLA4 and to other mannosylated dextran drug delivery vehicles that deliver other small molecule payloads, as for example DTPA loaded with copper (Example 1).

Infectious Diseases:

In addition to cancer, CD206+ M2-like macrophages are important contributors to the pathobiology of numerous infectious diseases. Repolarization of macrophages from a M2-like to a M1-like activated phenotype may have a therapeutic effect in persons with these illnesses. Examples may include Dengue Fever, which is caused by a vector borne Flavivirus, tuberculosis, which is a bacterial infection, and leishamiasis, which is a protozoan infection. All of these pathogens replicate in CD206+ macrophages and/or enter these cells via interactions with CD206. Human Immunodeficiency Virus (HIV) causes Acquired Immunodeficiency Syndrome (AIDS). In current practice, HIV viremia and many of the symptoms of AIDS can be controlled by combined antiretroviral therapy (cART). However, persistent cART resistant cellular reservoirs exist in patients treated with cART preventing curative treatment with cART. An important cART resistant reservoir is comprised of CD206+ macrophages. Finally, CD206+ macrophages contribute the pathobiology of several parasitic worms.

What is claimed is:

1. A method for repolarizing a tumor associated macrophage (TAM) from an immunosuppressive (M2-like) phenotype to a proinflammatory (M1-like) phenotype comprising administering to a subject in need thereof an effective dose of a compound, wherein the compound is Formula (I);

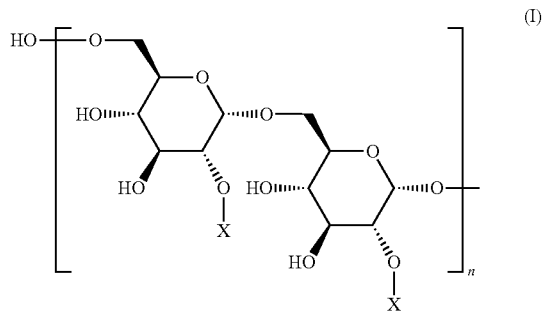

wherein
each X is independently H, L1-A, or L2-R;
each L1 and L2 are independently an amino-terminated leash;
each A independently is H or a therapeutic agent bound to the amine-terminated leash, wherein the amino-terminated leash has the formula —(CH$_2$)$_p$S(CH$_2$)$_q$—NH— with an optional attachment with amide, amidine, and/or hydrazone group, wherein p and q are integers from 0 to 5, wherein the therapeutic agent is selected from the group consisting of paclitaxel, gemcitabine, lapitinib, doxorubicin, and a bisphophonate;
each R indepedently is mannose, fucose, n-acetylglucosamine, or H;
and n is an integer greater than zero,
wherein at least one A is the therapeutic agent, and at least one R is mannose.

2. The method of claim 1, wherein the therapeutic agent is selected from: the paclitaxel, gemcitabine, lapatinib, and doxorubicin.

3. The method of claim 2, wherein the therapeutic agent is the doxorubicin.

4. The method of claim 2, wherein administration of the compound to the subject has reduced toxicity relative to an equivalent dose of the therapeutic agent not conjugated to the compound.

5. The method of claim 1, wherein the therapeutic agent is the bisphosphonate.

6. The method of claim 5, wherein the bisphosphonate is zoledronic acid.

7. The method of claim 1, wherein the compound is administered in conjunction with at least one other therapy or treatment and, wherein the at least one other treatment or therapy is a chemotherapy, radiation therapy, or immunotherapy.

8. The method of claim 7, wherein the at least one other treatment or therapy is anti-CTLA4 immunotherapy.

9. The method of claim 7, wherein the combined administration of the compound and the at least one treatment or therapy provides greater efficacy or is synergistically effective relative to administration of either alone.

* * * * *